US006355464B1

(12) United States Patent
Healy et al.

(10) Patent No.: US 6,355,464 B1
(45) Date of Patent: Mar. 12, 2002

(54) *M. TUBERCULOSIS* RNA POLYMERASE ALPHA SUBUNIT

(75) Inventors: Judith M. Healy, Lexington; Jana Bodorova, Rockville; Kelvin T. Lam, Belmont; Andrea J. Lesoon, Cambridge, all of MA (US)

(73) Assignee: Anadys Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/180,827

(22) PCT Filed: Dec. 3, 1997

(86) PCT No.: PCT/US97/22216

§ 371 Date: Jan. 1, 1999

§ 102(e) Date: Jan. 1, 1999

(87) PCT Pub. No.: WO98/24891

PCT Pub. Date: Jun. 11, 1998

Related U.S. Application Data

(60) Provisional application No. 60/032,292, filed on Dec. 3, 1996.

(51) Int. Cl.$^7$ .......................... C12N 9/12; C12N 15/00; C07H 21/04

(52) U.S. Cl. ...................... 435/194; 435/15; 435/252.3; 435/254.11; 435/325; 435/348; 435/320.1; 435/410; 536/23.2; 536/23.1; 536/23.7

(58) Field of Search ................................ 435/15, 252.3, 435/254.11, 325, 348, 320.1, 194, 410; 536/23.2, 23.7

(56) References Cited

U.S. PATENT DOCUMENTS 5,786,147 A * 7/1998 Mabilat et al. ................ 435/6

OTHER PUBLICATIONS

Harshey et al., *Biochimica et Biophysica Acta*, 432:49–59, 1976.

Miller et al., *Antimicrobial Agents and Chemotherapy*, 38:805–811, 1994.

* cited by examiner

*Primary Examiner*—Rebecca E. Prouty
*Assistant Examiner*—Richard Hutson
(74) *Attorney, Agent, or Firm*—Darby & Darby

(57) ABSTRACT

The present invention provides isolated nucleic acids encoding RNA polymerase alpha subunit from *M. tuberculosis,* vectors comprising the nucleic acids, cells comprising the vectors, and methods for producing *M. tuberculosis* alpha subunit. The invention also provides in vitro and in vivo methods for high-throughput screening to identify inhibitors of *M. tuberculosis* RNA polymerase.

5 Claims, 8 Drawing Sheets

```
  1 cgagtaccccacacttcggggcgccgccccgagtgccccacagacgtcatatggcgacgtcgaaaggaagaagaaa  80

81 cacc ATG CTG ATC TCA CAG CGC CCC ACC CTG TCC GAG GAC GTC CTC ACC GAC AAC CGA TCC  141
  1      M   L   I   S   Q   R   P   T   L   S   E   D   V   L   T   D   N   R   S   19

142 CAG TTC GTG ATC GAA CCG CTG GAG CCG GGA TTC GGC TAC ACC CTG GGC AAT TCG CTG CGT  201
 20  Q   F   V   I   E   P   L   E   P   G   F   G   Y   T   L   G   N   S   L   R   39

202 CGC ACC CTG CTG TCG ATT CCC GGA GCG GCC GTC ACC AGC ATT CGC ATC GAT GGT GTA  261
 40  R   T   L   L   S   I   P   G   A   A   V   T   S   I   R   I   D   G   V   59

262 CTG CAC GAA TTC ACC ACG GTG CCC GGG GTC AAA GAA GAT GTC ACC GAG ATC ATC CTG AAT  321
 60  L   H   E   F   T   T   V   P   G   V   K   E   D   V   T   E   I   I   L   N   79

322 CTC AAG AGC CTG GTG GTG TCC TCG GAG GAG GAG CCG GTC ACC ATG TAC CTA CGC AAG  381
 80  L   K   S   L   V   V   S   S   E   E   D   E   P   V   T   M   Y   L   R   K   99

382 CAG GGT CCG GGT GAG GTT ACC CAC ATC GCC ACG GCC GAC ATC GTG CCG CCG AAG GGC CTC GAG GTC CAC  441
100  Q   G   P   G   E   V   T   H   I   A   T   A   D   I   V   P   P   K   G   L   E   V   H   119

442 AAC CCC GGC ATG CGT GGC TAT GTC AAC GAT CTG AAC CGG CAA AAC CGG GCT TCG GCC GAA ATT  501
120  N   P   G   M   R   G   Y   V   N   D   L   N   R   Q   N   R   A   S   G   A   E   I   139

502 GTC GAG CGT GGC CGC GCC ATT CCA GTC TAC TCA CCG GTG CTC AAA GTG ACC TAC AAG GTG GAC  561
140  V   E   R   G   R   A   I   P   V   Y   S   P   V   L   K   V   T   Y   K   V   D   159

562 GGG CGC ATT CCA GTC TAC TCA CCG GTG CTC AAA GTG ACC TAC AAG GTG GAC  621
160  G   R   I   P   V   Y   S   P   V   L   K   V   T   Y   K   V   D   179
```

FIG. 3B

```
622  GCC ACC CGG GTC GAG CAG CGC ACC GAC TTC GAC AAG CTG ATC CTG GAC GTG GAG ACC AAG  681
180   A   T   R   V   E   Q   R   T   D   F   D   K   L   I   L   D   V   E   T   K   199

682  AAT TCA ATC AGC CCG CGC GAC GCG CTG GCG TCG GCT GGC AAG ACG CTG GTC GAG TTG TTC  741
200   N   S   I   S   P   R   D   A   L   A   S   A   G   K   T   L   V   E   L   F   219

742  GGC CTG GCA CGG GAA CTC AAC GTC GAA GCC ATC GAA GGC ATC GAG ATC GGG CCG TCG CCG GCC  801
220   G   L   A   R   E   L   N   V   E   A   E   G   I   E   I   G   P   S   P   A   239

802  GAG GCC GAT CAC ATT GCG TCA TTC GCG CTG CCG ATC GAC GAC CTG GAT CTG ACG GTG CGG  861
240   E   A   D   H   I   A   S   F   A   L   P   I   D   D   L   D   L   T   V   R   259

862  TCC TAC AAC TGC CTC AAG CGC GAG GGG GTG CAC ACC GTG GGC GAA CTG GTG GCG CGC ACC  921
260   S   Y   N   C   L   K   R   E   G   V   H   T   V   G   E   L   V   A   R   T   279

922  GAA TCC GAC CTG CTT GAC ATC CGC AAC TTC GGT CAG AAG TCC ATC GAC GAG GTG AAG ATC  981
280   E   S   D   L   L   D   I   R   N   F   G   Q   K   S   I   D   E   V   K   I   299

982  AAG CTG CAC CAG CTG GGC CTG TCA CTC AAG GAC AGC CCG CCG AGC TTC GAC CCC TCG GAG  1041
300   K   L   H   Q   L   G   L   S   L   K   D   S   P   P   S   F   D   P   S   E   319

1042 GTC GCG GGC TAC GAC GTC GCC ACC TGG TCG ACC GGC GAG GGC GCG TAC GAC GAG CAG  1101
320   V   A   G   Y   D   V   A   T   W   S   T   E   G   A   Y   D   E   Q   339

1102 GAC TAC GCC GAA ACC GAA CAG CTT TAG actgcctctaatccagacaggagcgtcagtatgcccaagcc  1170
340   D   Y   A   E   T   E   Q   L   *                                              348
```

M. TUBERCULOSIS RNA POLYMERASE ALPHA SUBUNIT

This application is a 371 of PCT/US97/22216, filed Dec. 3, 1997, which claims the benefit of Ser. No. 60/032,292 filed Dec. 3, 1996.

FIELD OF THE INVENTION

The present invention relates to novel nucleic acids encoding RNA polymerase alpha subunit from *M. tuberculosis* and methods for use thereof.

BACKGROUND OF THE INVENTION

The intracellular pathogen *Mycobacterium tuberculosis* is the causative agent of tuberculosis in humans and is responsible for millions of deaths worldwide each year (Bloom et al. *Science* 257:1055, 1992). The emergence of multidrug resistant forms of tuberculosis has mandated the development of new antibiotics effective against refractory *M. tuberculosis* strains. Novel drugs which, like rifampin (Vall-Spinosa et al., *N. Eng. J. Med.* 283: 616, 1970), may be capable of inhibiting the prokaryotic transciptional machinery, could contribute significantly to the development of therapies to combat *M. tuberculosis.*

The RNA polymerase of eubacteria consists of four subunits (α, β, β', and σ) and exists in two major forms: core enzyme ($\alpha_2$, β, β') and holoenzyme ($\alpha_2$, β, β' plus one of several σ subunits) (Chamberlin, in *RNA Polymerase,* Losick et al., eds., Cold Spring Harbor, 1976, pp. 17–67). The α subunit contains determinants for protein-protein interactions with transcription activators and protein-DNA interaction with upstream elements (Ishihama, *Mol.Microbiol.* 6:3283, 1992; Russo et al., *J. Biol.Chem.* 267:14515, 1992; Ebright et al., *Curr.Opin.Genet.Dev.* 5:197, 1995). The amino terminal domain of α is also required for assembly of the multisubunit core RNA polymerase (Ishihama, *Adv. Biophys.* 14:1, 1981). The β subunit is essential for transcript initiation and elongation, which β' apparently functions in binding of the core enzyme to template DNA (Yura et al., *Ann.Rev.Genet.* 13:59, 1979). Core RNA polymerase is capable of RNA synthesis; however, σ is required for specific initiation of transcripts at promoter sequences (Gross et al., in *Transcriptional Regulation,* Cold Spring Harbor, 1992, pp. 129–176).

Discovery of inhibitors of *M. tuberculosis* RNA polymerase is hampered by a lack of information concerning components of the *M. tuberculosis* transcriptional apparatus, difficulties in obtaining sufficient yields of active enzymes for biochemical studies, and biosafety concerns. Establishment of an in vitro transcription system employing purified and reconstituted RNA polymerase would greatly advance efforts to identify new therapeutic agents active against tuberculosis.

Accordingly, there is a need in the art for compositions and methods utilizing cloned genes and purified proteins derived from *M. tuberculosis* RNA polymerase.

SUMMARY OF THE INVENTION

The present invention is based on the isolation and characterization of DNA encoding the a subunit of RNA polymerase derived from *M. tuberculosis.* In one aspect, the invention provides a purified, isolated nucleic acid having SEQ. I.D. No. 4 the sequence shown in FIG. 3. The invention also encompasses sequence-conservative and function-conservative variants of this sequence. The invention also provides vectors comprising these sequences, and cells comprising the vectors.

In another aspect, the present invention provides a purified, isolated polypeptide encoded by the nucleic acid SEQ. I.D. No. 5 sequence shown in FIG. 3, as well as function-conservative variants thereof. In one embodiment, the invention provides a purified α subunit further comprising a hexahistidine tag. The invention also provides purified, reconstituted core- and holoenzyme comprising the α subunit.

In yet another aspect, the invention provides in vitro methods for high-throughput screening to detect inhibitors of *M. tuberculosis* RNA polymerase. In one embodiment, the methods comprise:

a) providing a mixture comprising
   (i) purified *M. tuberculosis* RNA polymerase and
   (ii) a DNA template encoding a promoter sequence that is recognized by *M. tuberculosis* RNA polymerase;
b) incubating the mixture in the presence of test compounds to form test samples, and in the absence of test compounds to form control samples, under conditions that result in RNA synthesis in the control samples;
c) measuring RNA synthesis directed by said *M. tuberculosis*-recognized promoter in the test and control samples; and
d) comparing the RNA synthesis detected in step (c) between the test and control samples. According to the invention, an RNA polymerase inhibitor is a test compound that causes a reduction in RNA synthesis directed by the *M. tuberculosis*-recognized promoter measured in the test sample relative to RNA synthesis measured in the control sample. In a preferred embodiment, the purified RNA polymerase used in practicing this method comprises recombinant subunits which are reconstituted to form an enzymatically active holoenzyme. In another embodiment, the ability of test compounds to bind to purified α subunit is monitored.

In yet another aspect, the invention provides in vivo methods for high-throughput screening to detect inhibitors of *M. tuberculosis* RNA polymerase. The methods are carried out by the steps of:

a) providing a non-mycobacterial bacterial strain, preferably *E. coli,* that
   (i) has been transformed with a DNA template encoding a promoter sequence that is recognized by *M. tuberculosis* RNA polymerase, and
   (ii) expresses enzymatically active *M. tuberculosis* RNA polymerase (e.g., $\alpha_2$, β, β' plus one of several σ subunits);
b) incubating the bacterial strain of (a) in the presence of test compounds to form test samples, and in the absence of test compounds to form control samples;
c) measuring RNA synthesis directed by said *M. tuberculosis*-recognized promoter in the test and control samples; and
d) comparing the RNA synthesis directed by said *M. tuberculosis*-recognized promoter detected in step (c) between the test and control samples. According to the invention, an RNA polymerase inhibitor is a test compound that causes a reduction in RNA synthesis measured in the test sample relative to RNA synthesis measured in the control sample.

These and other aspects of the present invention will be apparent to those of ordinary skill in the art in light of the present specification and appended claims.

BRIEF DESCRIPTION OF THE DRAWINGS

Figure 1:
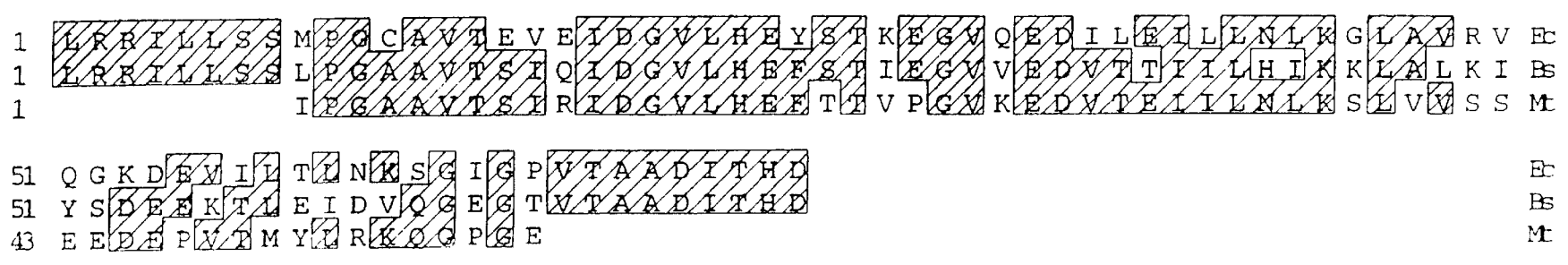

FIG. 1 is a graphic illustration comparing the deduced amino acid sequence of the M. tuberculosis rpoA gene fragment SEQ. I.D. No. 1 and corresponding regions of α subunits of *B. subtilis* and *E. coli.* Mt,SEQ. I.D. No. 3 *M. tuberculosis;* Bs, *B. subtilis;* Ec, *E. coli.* Dashed lines denote conserved segments of *B. subtilis* and *E. coli* proteins for which oligonucleotides were designed.

FIG. 2A is a photographic illustration of a Southern blot analysis of rpoA hybridizing cosmid clones. Four different positive clones (designated IIA5, IIA3, ID9, and IC5) isolated from an *M. tuberculosis* cosmid library were digested with NotI and hybridized with an rpoA gene probe. Sizes of DNA markers (λ EcoT141, Amersham) are indicated in kb.

FIG. 2B is a photographic illustration of a Southern blot analysis of rpoA hybridizing cosmid clones, showing structural conservation of genomic and cosmid-borne rpoA sequences. Purified cosmid IC5 DNA (lanes 1–5) or *M. tuberculosis* H37Rv genomic DNA (lanes 7–11) were digested with the indicated restriction enzymes and hybridized with an rpoA probe. Sizes of DNA markers (λ EcoT141, Amersham) are indicated in kb.

FIG. 3A and FIG. 3B shows the nucleotide SEQ. I.D. No.4 and deduced amino acid SEQ. I.D. No. 5 sequences of the *M. tuberculosis* H37Rv rpoA gene. RBS denotes a potential ribosome binding site. The putative start and stop codons of the rpoA gene product are at 85–87 and 1126–1128, respectively.

Figure 4A:
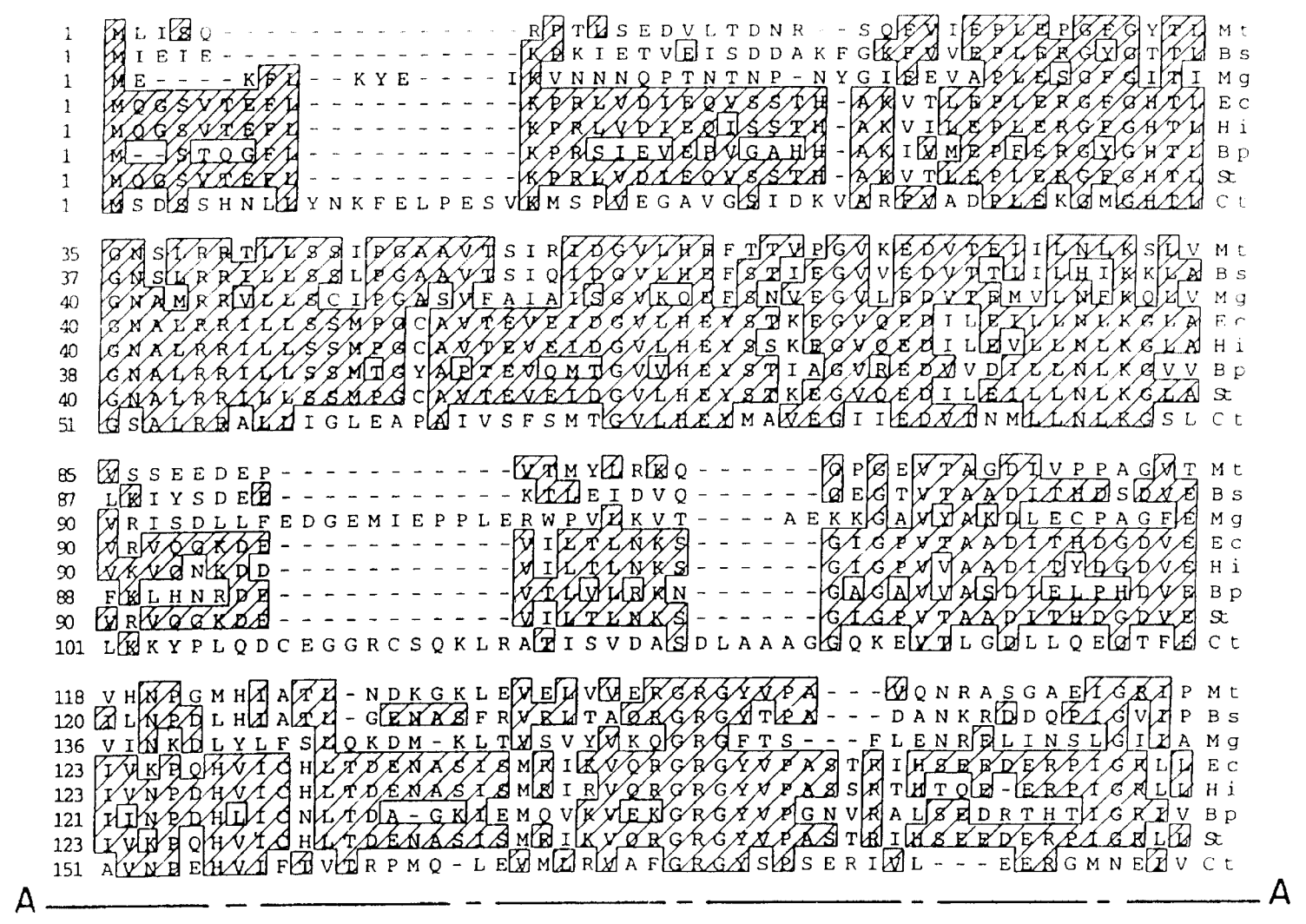
Figure 4B:
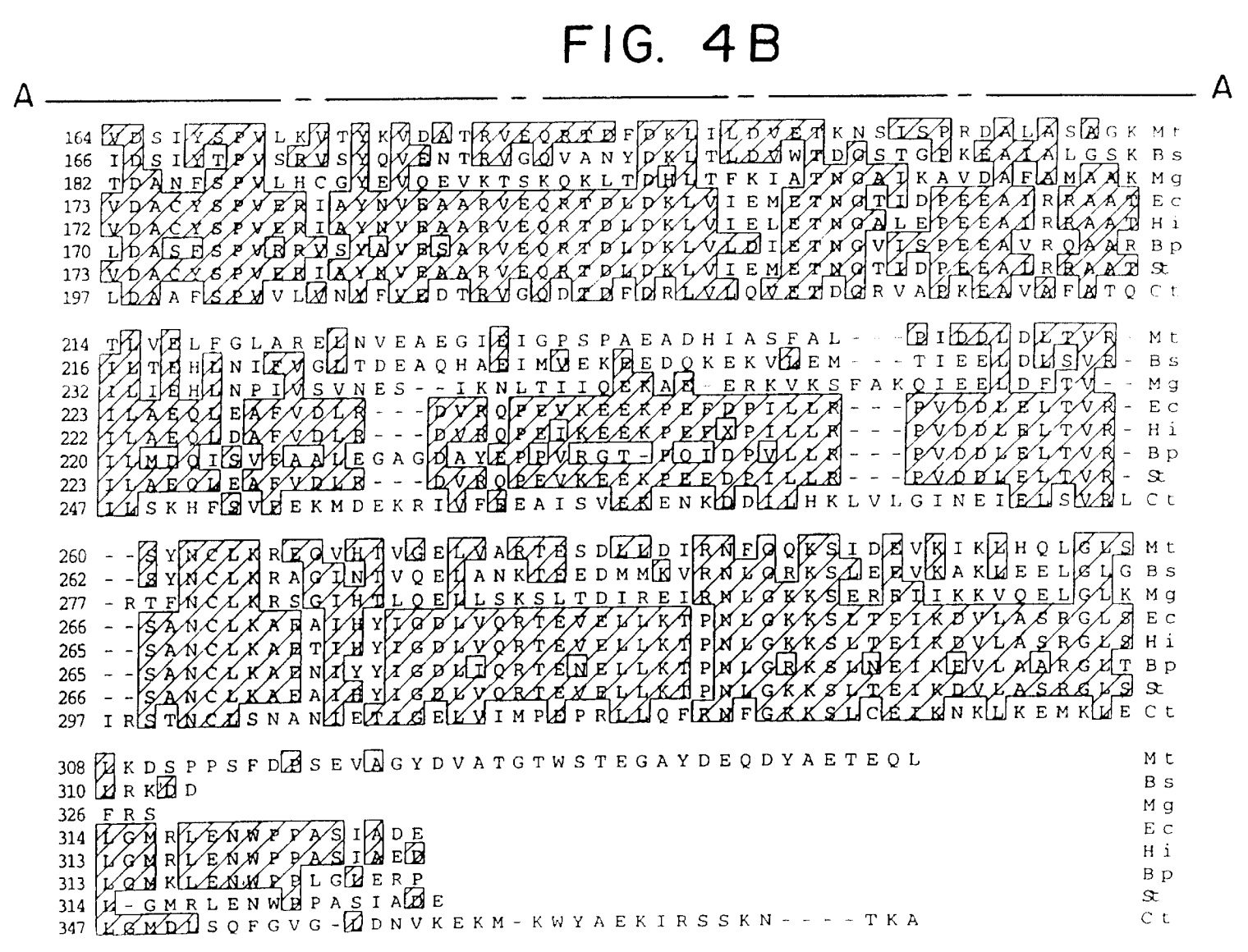

FIG. 4A and FIG. 4B is a graphic illustration comparing the inferred amino acid sequence of the *M. tuberculosis* H37Rv α subunit with SEQ. I.D. No. 4 sequences of α subunits from other bacteria. *B. subtilis* (Bs), SEQ. I.D. No. 6 *M. genitalium* (Mg), SEQ. I.D. No. _b 7*E. coli* (Ec), SEQ. I.D. No. 8 *H. influenza* (Hi), SEQ. I.D. No. 9 *B. pertusis* (Bp), SEQ. I.D. No. 10 *S. typhimurium* (St), SEQ. I.D. No. 11 and *C. trachomitis* (Ct) SEQ. I.D. No. 12. Shading indicates identical amino acid residues. Amino acid sequence alignments were performed using MegAlign (DNAStar).

FIG. 5 is a photographic illustration of an SDS-polyacrylamide gel electropherogram depicting the expression and purification of *M. tuberculosis* a subunit in *E. coli.* Lane 1 shows molecular mass markers (kDa); lanes 2 and 3 show total proteins from uninduced and IPTG-induced cultures, respectively, of *E. coli* harboring pJH37; and lane 4 shows purified *M. tuberculosis* α subunit (approximately 38 kDa), which is indicated by an arrow.

FIG. 6 is a photographic illustration of an SDS-polyacrylamide gel electropherogram showing the reconstitution and purification of core- and holo-RNA polymerase from *M. tuberculosis.* Lanes 1 and 6 show molecular mass markers (kDa); lane 2 shows a-histidine-containing core enzyme; lane 3 shows a histidine-containing holoenzyme; lane 4 shows N-terminal histidine-tagged primary sigma; and lane 5 shows purified *E. coli* holoenzyme.

FIG. 7 is a graphic illustration of in vitro transcription reactions employing reconstituted purified *M. tuberculosis* RNA polymerase holoenzyme and T101 and T125 promoter-containing DNA templates.

DETAILED DESCRIPTION OF THE INVENTION

All patent applications, patents and literature references cited herein are hereby incorporated by reference in their entirety. In the case of inconsistencies the present disclosure will prevail.

The present invention is based on the isolation of a fragment of the *M. tuberculosis* rpoA gene, encoding the α subunit of RNA polymerase. As described in Example 1 below, the fragment was isolated by the polymerase chain reaction (PCR) using primers directed against regions of a that are highly conserved among Gram-positive and Gram-negative bacteria. The amplified DNA was utilized as a hybridization probe to recover the entire rpoA gene from a cosmid library of genomic DNA from virulent *M. tuberculosis* strain H37RV. Nucleotide sequencing indicated that the 1044 bp *M. tuberculosis* rpoA open reading frame (ORF) encodes a protein of 347 amino acids which shows significant structural similarity to the α subunits of diverse bacterial species with greatest identity to the *B. subtilis* α protein (FIG. 1).

Though structurally conserved throughout most of its length, the inferred amino acid sequence of the *M. tuberculosis* α subunit diverged from that of *B. subtilis* and other bacteria at its extreme C-terminus. Interestingly, studies on *E. coli* RNA polymerase subunits have indicated that the C-terminal 94 residues of α function in interactions with certain transcriptional regulatory proteins, while the N-terminal domain may play a more highly conserved role in facilitating the core assembly (Ishihama, *Mol.Microbiol.* 6:3283, 1992; Russo et al., *J.Biol.Chem.* 267:14515, 1992).

The *B. subtilis* rpoA gene is part of a large operon that is cotranscribed with genes for initiation factor 1 and ribosomal proteins B, S13, S11 , and L17; and, unlike the pattern of gene organization seen in *E. coli* the *B. subtilis* rpoA gene cluster is genetically linked to the rpoB-C operon encoding RNA polymerase components β and β' (Boylan et al., *J.Bacteriol.* 171:2553, 1992).

In practicing the present invention, many techniques in molecular biology, microbiology, recombinant DNA, and protein biochemistry such as these explained fully in, for example, Sambrook et al., 1989, *Molecular Cloning: A Laboratory Manual,* Second Edition, Cold Spring Harbor Laboratory Press, Cold Spring Harbor, New York; *DNA Cloning: A Practical Approach,* Volumes I and II, 1985 (D. N. Glover ed.); *Oligonucleotide Synthesis,* 1984, (M. L. Gait ed.); *Transcription and Translation,* 1984 (Hames and Higgins eds.); *A Practical Guide to Molecular Cloning;* the series, *Methods in Enzymology* (Academic Press, Inc.); and *Protein Purification: Principles and Practice,* Second Edition (Springer-Verlag, N.Y.), may be used.

The present invention encompasses nucleic acid sequences encoding the α subunit of *M. tuberculosis* RNA polymerase, enzymatically active fragments derived therefrom, and related sequences. As used herein, a nucleic acid that is "derived from" a sequence refers to a nucleic acid sequence that corresponds to a region of the sequence, sequences that are homologous or complementary to the sequence, and "sequence-conservative variants" and "function-conservative variants". Sequence-conservative variants are those in which a change of one or more nucleotides in a given codon position results in no alteration in the amino acid encoded at that position. Function-conservative variants are those in which a given amino acid residue in the α subunit has been changed without altering the overall conformation and function of the polypeptide, including, but not limited to, replacement of an amino acid with one having similar physico-chemical properties (such as, for example, acidic, basic, hydrophobic, and the like). Fragments of the α subunit that retain enzymatic activity can be identified according to the methods described herein, such as e.g., expression in *E. coli* followed by enzymatic assay of the cell extract or by purification and reconstitution of the purified polypeptide into an enzymatically active holoenzyme.

The nucleic acids of the present invention include purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. The nucleic acids may be isolated directly from cells. Alternatively, PCR can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

Figure 2A:
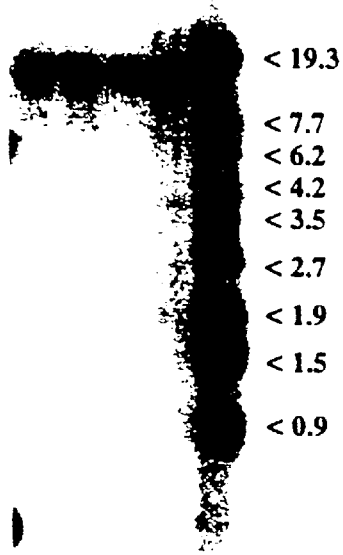
Figure 2B:
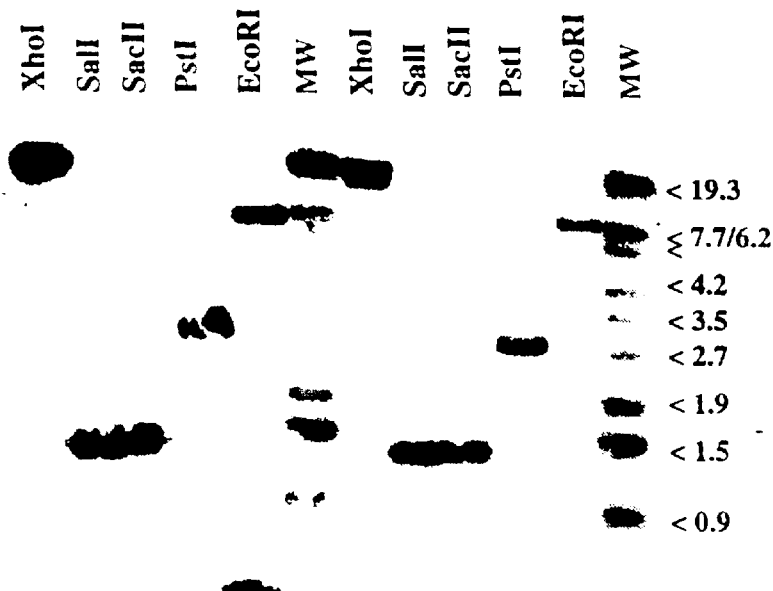

The nucleic acids of the present invention may be flanked by natural *M. tuberculosis* regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed α subunit sequences or derivatives or fragments thereof. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Suitable host cells may be transformed/transfected/infected as appropriate by any suitable method including electroporation, $CaCl_2$ mediated DNA uptake, fungal infection, microinjection, microprojectile, or other established methods.

Appropriate host cells include bacteria, archebacteria, fungi, especially yeast, and plant and animal cells, especially mammalian cells. Of particular interest are *E. coli, B. subtilis, Saccharomyces cerevisiae, Saccharomyces carlsbergensis, Schizosaccharomyces pombi,* SF9 cells, C129 cells, 293 cells, Neurospora. and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced Mycobacterial-derived peptides and polypeptides.

Advantageously, vectors may also include a transcription regulatory element (i.e., a promoter) operably linked to the α subunit portion. The promoter may optionally contain operator portions and/or ribosome binding sites. Non-limiting examples of bacterial promoters compatible with *E. coli* include: trc promoter, β-lactamase (penicillinase) promoter; lactose promoter; tryptophan (trp) promoter; arabinose BAD operon promoter; lambda-derived P1 promoter and N gene ribosome binding site; and the hybrid tac promoter derived from sequences of the trp and lac Uv5 promoters. Non-limiting examples of yeast promoters include 3-phosphoglycerate kinase promoter, glyceraldehyde-3-phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

Nucleic acids encoding wild-type or variant α subunit polypeptides may also be introduced into cells by recombination events. For example, such a sequence can be introduced into a cell, and thereby effect homologous recombination at the site of an endogenous gene or a sequence with substantial identity to the gene. Other recombination-based methods, such as non-homologous recombinations or deletion of endogenous genes by homologous recombination, may also be used.

α subunit-derived polypeptides according to the present invention, including function-conservative variants, may be isolated from wild-type or mutant *M. tuberculosis* cells, or from heterologous organisms or cells (including, but not limited to, bacteria, fungi, insect, plant, and mammalian cells) into which an α subunit-derived protein-coding sequence has been introduced and expressed. Furthermore, the polypeptides may be part of recombinant fusion proteins (see, e.g., Example 2 below). Alternatively, polypeptides may be chemically synthesized by commercially available automated procedures, including, without limitation, exclusive solid phase synthesis, partial solid phase methods, fragment condensation or classical solution synthesis.

"Purification" of an α subunit polypeptide refers to the isolation of the polypeptide in a form that allows its enzymatic activity to be measured without interference by other components of the cell in which the polypeptide is expressed. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the α subunit or against peptides derived therefrom can be used as purification reagents. Other purification methods are possible.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Screening Methods to Identify Anti-tuberculosis Agents

The methods and compositions of the present invention can be used to identify compounds that inhibit the function of M. tuberculosis RNA polymerase and thus are useful as anti-tuberculosis agents. This is achieved by providing enzymatically active recombinant α subunit according to the present invention, in combination with other components of RNA polymerase, in a context in which the inhibitory effects of test compounds can be measured. Alternatively, the ability of test compounds to bind to purified α subunit is monitored, using methods well-known in the art. Test compounds identified using the methods of the invention encompass those that interfere with the enzymatic activity of RNA polymerase and/or disrupt the interaction of the α subunit with transcriptional activators. Thus, the compounds may function as general or gene-specific transcriptional inhibitors.

In a preferred embodiment, recombinant *M. tuberculosis* RNA polymerase subunits (α, β, β' plus one of several α subunits) are purified in milligram quantities from *E. coli* cultures by affinity methods utilizing a hexahistidine tagged α subunit. Enzymatically active holoenzyme is reconstituted using these components (see, e.g., Example 2 below). The active polymerase is then incubated in the presence of test compounds to form test mixtures, and in the absence of test compounds to form control mixtures. In vitro transcription is then carried out using a DNA template containing appropriate promoter sequences (see, e.g., Example 2 below).

In another embodiment, *M. tuberculosis* RNA polymerase subunits ($\alpha_2$, β, β' plus one of several σ subunits) are co-expressed in *E. coli* or another surrogate bacterial cell, in conjunction with an appropriate promoter functionally linked to a reporter gene. The ability of test compounds to differentially inhibit *M. tuberculosis* RNA polymerase is then assessed by measuring the amount and/or activity of the reporter gene product.

*M. tuberculosis* promoters useful in practicing the invention include without limitation: P1 or P2 hsp 60 promoters (Stover et al., *Nature* 351:456, 1991); cpn-60 promoter (Kong et al., *Proc.Natl.Acad.Sci. USA* 90:2608, 1993); 85A antigen promoter (Kremer, *J. Bacteriol.* 177:642, 1995); PAN promoter (Murray et al., *Mol. Microbiol.* 6:3331, 1992); 16S RNA promoter (Ji et al., *Microbiol.* 140: 2829, 1994); and askβ promoter (Cirillo et al., *Mol. Microbiol.* 11:629, 1994). Useful reporter genes include without limitation xylE (Curcic et al., *Mol. Microbiol* 13:1057, 1994); CAT (Das Gupta et al., *J. Bacteriol.* 175:5186, 1993); luciferase (Cooksey et al., *Antimicrob.Agts.Chemother.* 37:1348, 1993); green fluorescent protein (Dhadayuthap et al., *Mol. Microbiol.* 17:901, 1995); and lacZ (Silhavy et al., *Microbiol.Rev.* 49:398, 1985).

It will be understood that the present invention encompasses *M. tuberculosis* RNA polymerases containing any appropriate a factor, which is used in conjunction with a particular promoter that is recognized by RNA polymerase containing that σ factor. Non-limiting examples of useful σ factors include $\sigma^A$, $\sigma^B$, and $\sigma^F$ (Doushkan et al., 1995; DeMaio et al., *Gene* 165:67, 1995). The invention also encompasses the identification of additional promoters that are recognized by a particular σ subunit. This is achieved by providing a library of random *M. tuberculosis* gene fragments cloned upstream of an appropriate reporter gene (see above). The library is transformed into *M. tuberculosis* or *M. smegmatis* and reporter gene expression is measured. Alternatively, the library is transformed into another bacterial cell, such as, e.g., *E. coli,* which expresses *M. tuberculosis* RNA polymerase core subunits as well as a σ subunit of interest and cognate promoters that drive reporter gene expression. In yet another embodiment, expression of an *M. tuberculosis* σ factor confers new recognition properties on *E. coli* RNA polymerase and permits isolation of promoters utilized specifically by a particular *M. tuberculosis* σ subunit.

Preferably, both in vitro and in vivo screening methods to detect *M. tuberculosis*-specific RNA polymerase inhibitors are adapted to a high-throughput format, allowing a multiplicity of compounds to be tested in a single assay. Such inhibitory compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondelle et al., *TibTech* 14:60, 1996). preferably using automated equipment, to allow for the simultaneous screening of a multiplicity of test compounds.

Useful anti-tuberculosis compounds are identified as those test compounds that decrease tuberculosis-specific transcription. Once a compound has been identified by the methods of the present invention as an RNA polymerase inhibitor, in vivo and in vitro tests may be performed to further characterize the nature and mechanism of the inhibitory activity. For example, classical enzyme kinetic plots can be used to distinguish, e.g., competitive and non-competitive inhibitors.

Compounds identified as RNA polymerase inhibitors using the methods of the present invention may be modified to enhance potency, efficacy, uptake, stability, and suitability for use in pharmaceutical formulations, etc. These modifications are achieved and tested using methods well-known in the art.

The present invention is further described in the following examples which are intended to further describe the invention without limiting the scope thereof.

EXAMPLE 1
Isolation and Analysis of the *M. tuberculosis* rpoA Gene

The following experiments were performed in order to clone the gene encoding *M. tuberculosis* RNA polymerase α subunit. In these experiments, the following materials and methods were used.

A. Materials and Methods

PCR amplification: *M. tuberculosis* H37Rv genomic DNA (1 ng) was amplified in a 100 μl reaction containing: 10 mM Tris-HCl pH 8.3, 1.5 mM $MgCl_2$, 500 mM KCl, 2.5 U Taq polymerase (Beohringer-Mannheim), 0.2 mM dNTPs and oligonucleotide primers (1 μM each): 5'-CTACGCAAGCAGGGTCCGGGTGAG-3' and 5'-CTCACCCGGACCCTGCTTGCGTAG-3'. PCR was performed in an Omnigene thermocycler with 35 cycles of 94° C. for 1 min, 55° C. for 2 min, 72° C. for 1 min. The amplification product was gel-purified and ligated into vector pCR2.1 (Invitrogen).

Cosmid hybridizations: A transducing lysate of a cosmid library of *M tuberculosis* H37Rv genomic DNA in vector pYA3060 was used. Cosmid-bearing *E. coil* Φ2819T (Jacobs et al., *Infec.Immun.* 52:101, 1986) colonies representing roughly five genomic equivalents were individually picked to wells of sterile 96-well microliter dishes and propagated at 30° C. in Luria broth containing ampicillin at 30 μg/ml and thymidine at 50 μg/ml. Colonies were grown overnight at room temperature on the above media as nylon filter replicas of the library. Filters were processed for colony hybridization by standard methods and probe hybridizations performed as described below. Cosmid DNAs were purified using maxiprep columns (Qiagen).

Southern blot analysis: Restriction enzyme digests of *M. tuberculosis* H37Rv chromosomal or cosmid DNAs were resolved by electrophoresis on 1% TAE-agarose gels and blotted to nylon filters using standard methods. Probe labeling and hybridizations were performed using the Gene Images hybridization system (Amersham) essentially as described by the supplier except that hybridizations and washes were carried out at 70° C.

DNA sequencing and analysis: Plasmid templates for nucleotide sequencing were purified using RPM miniprep kits (Bio101). PCR cycle sequencing (ABI Prizm) was carried out with an Applied Biosystems automated sequencer.

B. Strategy for *M. tuberculosis* rpoA Gene Isolation

A fragment of the *M. tuberculosis* rpoA gene was isolated by PCR, using oligonucleotide primers SEQ. I.D. Nos. 13 and 14 homologous to defined regions of α that are conserved among Gram-positive and Gram-negative bacterial species. Amino acid sequence alignments of the α subunits of *B. subtilis* and *E. coli* SEQ. I.D. Nos. 2 and 3, revealed several short regions of identity clustered primarily within the N-terminal half of α implicated in association with RNA polymerase core subunits. Primers corresponding to conserved a segments LRRILLSS and VTAADITHD (amino acids 39–46 and 106–114, respectively of the *B. subtilis* subunit) specifically amplified a DNA fragment of anticipated size (228 bp) using *M. tuberculosis* H37Rv genomic DNA as a template. To confirm that the amplified DNA contained rpoA sequences, the 228 bp fragment was subcloned and a partial nucleotide sequence determined. The deduced amino acid sequence of the PCR product showed SEQ. I.D. No. 1 significant homology to the α subunits of other bacteria SEQ. I.D. Nos. 2 and 3 (FIG. 1), confirming its identity as an rpoA gene fragment. One ORF of the 228 bp fragment displayed high degree of identity to corresponding intervals of the *B. subtilis* (61%) and *E. coli* (55%) α subunits. The *M. tuberculosis* rpoA-derived sequence had an overall G+C content of 60% while the G+C content for bases occupying the third position of each codon increased to 76%, values in good agreement with compositions of other *M. tuberculosis* genes (Weiden et al., in *Tuberculosis,* Little, Brown, 1996, pp. 211–222).

C. Southern Blot Analvsis and Isolation of the Entire *M. tuberculosis* rpoA Gene To establish that the cloned 228 bp fragment was mycobacterial in origin, Southern blot analysis of restriction enzyme digests of *M. tuberculosis* H37Rv genomic DNA was performed. The PCR probe detected unique restriction fragments in chromosomal digests (FIG. 2B). These data are consistent with a single copy of the rpoA gene in the *M. tuberculosis* chromosome (two bands of hybridization observed in the EcoRI digest result from the presence of an EcoRI site within the 228 bp probe sequence). The full-length rpoA gene was obtained from a cosmid library of *M. tuberculosis* H37Rv genomic fragments using the 228 bp PCR probe. Screening of approximately 600 cosmid-bearing *E. coli* colonies (representing roughly 5 genome equivalents) with the rpoA gene fragment yielded 4 positive clones. Restriction analysis indicated that the 4 isolates differed from one another with respect to total insert size, though all shared a roughly 10 kb NotI fragment which hybridized to the rpoA gene probe (FIG. 2A). One rpoa-hybridizing cosmid clone, designated IC5, was chosen for further analysis. Southern blotting of IC5 DNA digested with a panel of restriction enzymes confirmed that the no gross structural rearrangements of the rpoA gene had occurred during cloning (FIG. 2B). The 1.4 kb SacII and 1.3 kb SalI rpoA-hybridizing fragments of cosmid IC5 were subcloned into vector pSKII+ prior to nucleotide sequencing.

D. Sequence Analysis of the *M. tuberculosis* rpoA Gene

Nucleotide sequencing was performed on plasmid subclones and on cosmid IC5 DNA. Nucleotide and deduced amino acid SEQ. I.D. Nos. 4 and 5 respectively sequences of the rpoA gene of *M. tuberculosis* are shown in FIGS. 3A and 3B. The sequence encodes a 1044 bp ORF which has an overall G+C composition of 63% (85% for bases occupying the codon third position). Assuming that the ATG at position 85–87 serves as the initiator codon, the ORF is expected to encode a protein of 347 amino acids. A strong match with the consensus sequence for an *M. tuberculosis* ribosome binding site (GAAAGGA), (Novick, in *Tuberculosis,* Little, Brown, 1996, pp. 187–198) is positioned just upstream of the putative ATG codon. Examination of more than 80 bp of nucleotide sequence upstream of the translation start site did not reveal regions of exact identity with prokaryotic promoter sites. Among α subunits studied in other bacterial species, the deduced amino acid sequence of the 347 residue *M. tuberculosis* protein SEQ. I.D. No. 5 displayed greatest similarity (48% identity) to the α subunit of the Gram-positive sporulating bacterium *B. subtilis* SEQ. I.D. No. 6 (FIGS. 4A and 4B).

EXAMPLE 2

Expression of *M. tuberculosis* RNA Polymerase α Subunit and Reconstitution of Active *M. tuberculosis* RNA Polymerase The following experiments were performed to purify *M. tuberculosis* RNA polymerase α subunit that had been expressed in *E. coli* and to reconstitute enzymatically active RNA polymerase holoenzyme.

A. Methods

Purification of *M. tuberculosis* α subunit: Recombinant α was produced in *E. coil* BL21(DE3) cells (Novagen) and grown at 37° C. in LB medium containing 25 µg/ml/ kanamycin. Overnight cultures (100 ml) were diluted 10-fold and grown in LB medium containing 25 µg/ml kanamycin until $A_{600}$=0.6 (approximately 75 min). Expression of α was induced for 3 hr with 4 mM IPTG. Purification of the α subunit was performd essentially as described by Tang, et. al, *Meth.Enzymol.* 273:130, 1996. Briefly, cell pellets were harvested by centrifugation for 10 min At 4° C. (3000×g). The pellet was resuspended in 20 ml buffer B (6 M guanidine HCl, 10 mM Tris (pH 7.9), 500 mM NaCl, 5 mM imidazole) and lysed by sonication. Inclusion bodies were removed by centrifugation at 42,000×g for 30 min at 4° C. The sample was then adsorbed onto $Ni^{2+}$-NTA (Qiagen) in buffer B. The sample was washed twice with 20 ml buffer B; washed twice with buffer B containing 30 mM imidazole; and eluted with 10 ml buffer B containing 500 mM imidazole. Adsorption, washes, and elution were performed with 1 min incubations at 4° C. with gentle mixing.

Reconstitution of α with other *M. tuberculosis* subunits to form core/holo-RNA polymerase: Reconstitution of core/ holo-enzyme was performed by combining 60, 300, and 600 µg of α, β, and β', respectively, followed slow removal of the denaturant by dialysis. The combined protein concentration was adjusted to 0.5 mg/ml with buffer B to prevent aggregation (Nobuyuki et al., *Meth.Enzymol* 273:121, 1996) and dialysed against buffer E (50 mM Tris (pH 7.9), 200 mM KCl, 10 mM $MgCl_2$, 10 µM $ZnCl_2$, 1 mM EDTA, 5 mM β-mercaptoethanol, 20% (v/v) glycerol) overnight at 4° C. Following dialysis, the sample was activated by incubation for 45 min at 30° C. and aggregates cleared by centrifugation at 10,000×g for 10 min at 4° C. The sample was adsorbed onto $Ni^{2+}$-NTA in buffer F (50 mM Tris (pH 7.9), 0.5 mM EDTA, 5% (v/v) glycerol), and washed three times in buffer F containing 5 mM imidazole, and eluted in buffer F containing 150 mM imidazole. Adsorption and elution were performed by incubating for 45 min at 4° C. and washes for 1 min. Each step was followed by centrifugation at 16,000×g for 2 min at 4° C. Core/holo-enzyme was dialysed in buffer F (50 mM Tris (pH 7.9), 50 mM KCl, 0.5 mM EDTA, 5% (v/v) glycerol) overnight at 4° C.

Purification of *M. tuberculosis* holoenzyme: Core polymerase and subassemblies were separated from holoenzyme by elution from a MonoQ column (Pharmacia) using a 0.2–0.5 M KCl gradient. Fractions containing holoenzyme were pooled and used the in vitro transcription assay.

Promoter construction: Recently, mycobacterium promoters have been cloned using a plasmid shuttle vector pSD7 (Das Gupta et al., *J. Bacteriol.* 175:5186, 1993) and in a later study, the strength of these promoters was analyzed (Bashyam et al., *J. Bacteriol.* 178:4847, 1996). Based on these studies two promoters, T125 and T101, identified as a weak and a strong promoter, respectively, were cloned into the pUC19 vector and used as templates for *M. tuberculosis* transcription asays.

Transcriptional activity: Holoenzyme was reconstituted by the addition of primary sigma factor MysA to the core polymerase and incubation at 30° C. for 20 minutes. The transcription reaction was performed as described (Shorenstein et al., *J. Biol.Chem.* 248:6170, 1973) except that 3 µg of template (pUC19, pMC116, or pMC117) was used per reaction containing a high salt transcription buffer (50 mM Tris (pH7.9), 10 $MgCl_2$, 200 mM KCl, 10 mM DTT, 0.1 mM EDTA, 1 mM $K_2HPO_4$ (pH7.5), 100 µg/ml BSA). 50 µl reactions were incubated for 30 minutes at 37° C. To precipitate the RNA transcripts and to stop the reaction, 100 µl of 10% TCA were added to the reaction. The TCA-precipitated RNA was adsorbed onto UniFilter GF/C (Packard, Meriden, Conn.) double-thick glass fiber filtermats using a cell harvester (Packard, Meriden, Conn.). The wells of the microtiter plate and the filter were washed two times with 5% TCA and bound radioactivity was determined using a TopCount-HTS (Packard, Meriden, Conn.) scintillation counter.

B. Results

Figure 5:
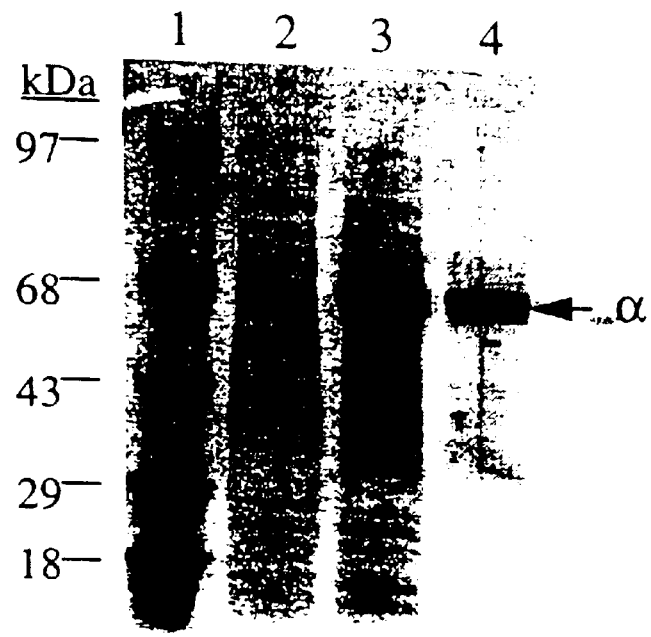

Recombinant *M. tuberculosis* α subunit was overproduced in soluble form in *E. coli* cells transformed with plasmid pJH37, a derivative of pET26b, containing the entire rpoA coding region. *M. tuberculosis* α was expressed at high levels as a C-terminal hexahistidine-tagged fusion protein and purified to homogeneity by affinity chromatography. The majority of the 6xHis-tagged α subunit was located in the soluble fraction and was further purified using a $Ni^{2+}$-NTA column. Elution of the α subunit polypeptide was performed using 0.5 M imidazole, resulting in >90% recovery of the subunits with >95% purity as estimated by SDS-PAGE (FIG. 5).

Figure 6:
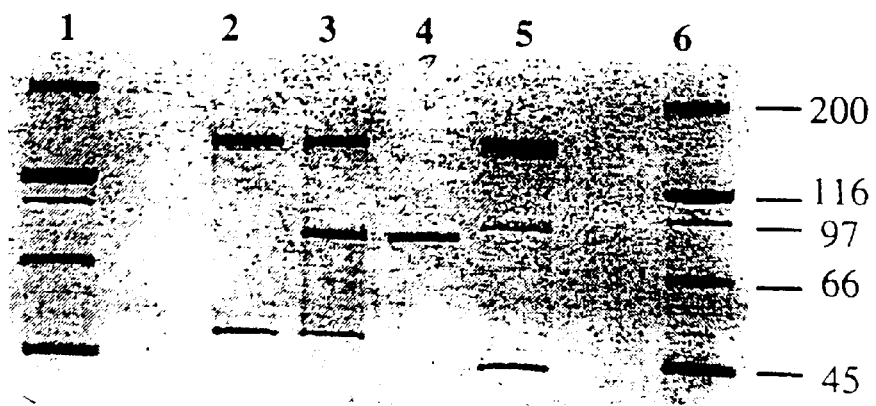

Core enzyme was reconstituted by combining crude preparations of the β and β' subunits with α polypeptide that contained a histidine tag, followed by removal of denaturant by dialysis to facilitate refolding. Holoenzyme was reconstituted by combining the core polymerase with purified primary σ (MysA) from *M. tuberculosis*. The core/ holoenzyme, containing a 6xHis tag on the α subunit, was purified from free subunits and subassemblies by batch elution from $Ni^{2+}$-NTA followed by elution from ion exchange chromatography (FIG. 6).

Figure 7:
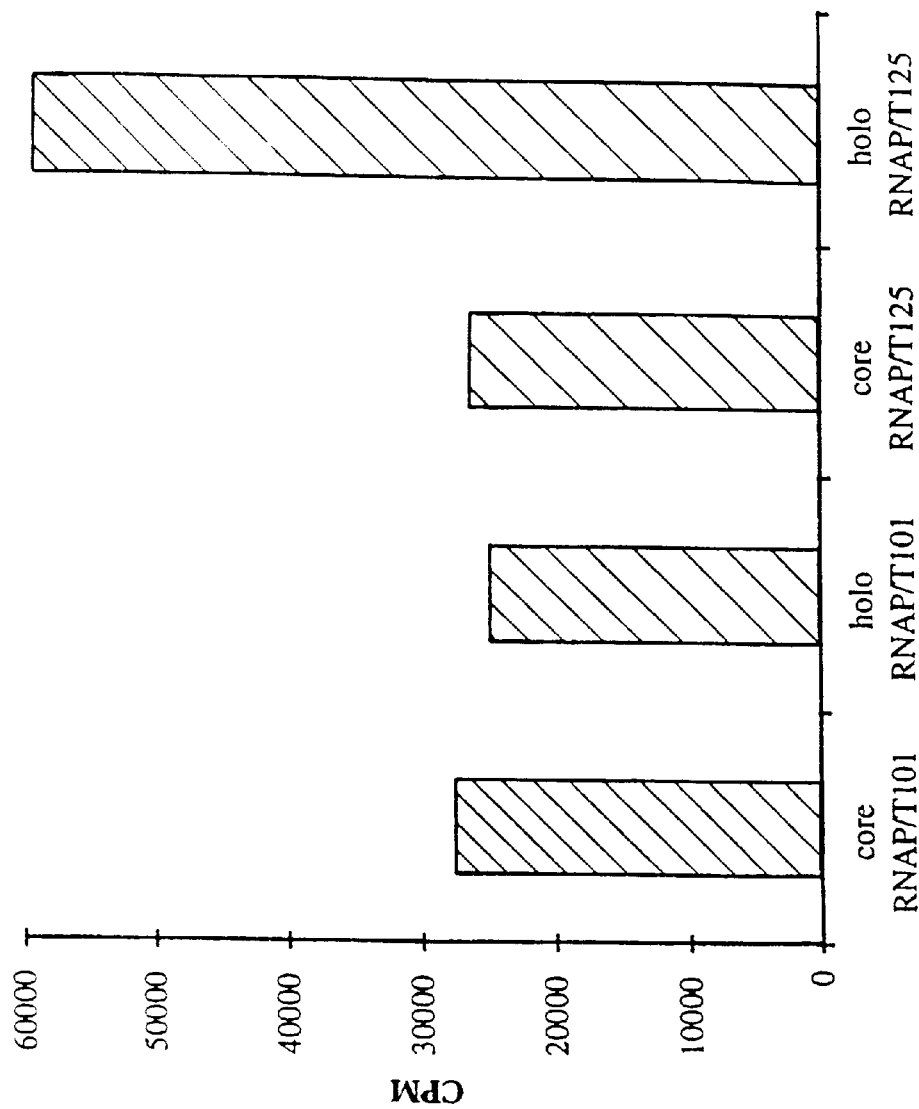

To demonstrate that reconstituted *M. tuberculosis* RNA polymerase possesses transcriptional activity, in vitro transcription reactions were performed using MysA-containing recombinant holoenzyme and templates containing two known MysA-dependent promoters (T101 and T125, which correspond to strong and weak mycobacterial promoters, respectively). The transcriptional activity of the reconstituted holoenzyme was more than two-fold higher when T101 was used as template as compared with T125 (FIG. 7), suggesting that the rate of transcription was related to both the strength of the promoter and to the particular σ factor used.

These experiments demonstrated that *M. tuberculosis* α subunit produced according to the invention can be purified and reconstituted into enzymatically active RNA polymerase holoenzyme that exhibits specificity for *M. tuberculosis* promoters.

EXAMPLE 3

High Throughput Screens for Inhibitors of *M. Tuberculosis* RNA Polymerase and α Subunit High-throughput screens for anti-tuberculosis agents may be performed using either an in vitro or in vivo format. In either case, the ability of test compounds to inhibit *M. tuberculosis* RNA polymerase-driven transcription of *M. tuberculosis* promoters is tested. Typically, a strong promoter such as T101 is used for the test reactions. The sequence of the T101 promoter is: identified by SEQ. ID. NO. 15 and read as follows.

T101:5'
AGCTTGCAGATCTAGCGATCGCAGC-
CGACGTGATACCTGACCGTTGTTGATA
GTGTCGGCGGCT-3' a) In vitro screens:

The following procedure is used for cell-free high-throughput screening. A Tomtec Quadra 96-well pipetting station is used to add the reaction components to polypropylene 96-well dishes. 5 μl aliquots of test compounds dissolved in DMSO (or DMSO alone as a control) are added to wells. This is followed by 20 μl of the RNA polymerase mixture, which consists of: 10 mM DTT, 200 mM KCl, 10 mM $Mg^{+2}$, 1.5 μM bovine serum albumin, and 0.25 μg reconstituted RNA polymerase. After allowing the test compound to interact with the RNA polymerase, 25 μl of the DNA/NTP mixture is added, containing: 1 μg template DNA (see above), 4 μM [α-$^{32}$P]-UTP, and 400 μM each CTP, ATP, and GTP.

After incubation for 30 min at 25° C., the reaction is stopped by addition of 150 μl 10% trichloroacetic acid (TCA). After incubation at room temperature for 60 min, the TCA-precipitated RNA is adsorbed onto double-thick glass fiber filtermats using a Tomtec cell harvester. The wells of the microtiter plate and the filter are washed twice with 5% TCA and bound radioactivity is determined usinjg a Wallac microbeta 1450 scintillation counter. Inhibitory activity due to the test compound is calculated according to the formula:

$$\% \text{ inhibition} = \frac{(cpm_{positive\ control} - cpm_{sample})}{cpm_{positive\ control}} \times 100$$

where $cpm_{positive\ control}$ represents the average of the cpm in wells that received DMSO alone, and $cpm_{sample}$ represents the cpm in the well that received test compound. Compounds that cause at least 50% inhibition are scored as positive "hits" in this assay.

As an additional control, rifampicin is used at a concentration of 30 nM, which results in a 50–75% inhibition of transcription in this assay.

b) In vivo screen:

M. tuberculosis RNA polymerase subunits (α, β, β', and a particular σ subunit) are expressed in E. coli under the control of regulatable promoters by transforming E. coli with appropriate plasmids. If the σ$^A$ subunit is expressed, a DNA sequence comprising the T101 promoter is also introduced into the cells to serve as a template for M. tuberculosis-specific transcription.

In one embodiment, the T101 promoter sequence is linked to a DNA sequence encoding the xylE gene product, catechol 2, 3-dioxygenase (CDO). When expressed in the E. coli cell, CDO converts catechol to 2-hydroxymuconic semialdehyde, which has a bright yellow color (having an absorbance maximum at 375 nm) that is easily detected in whole cells or in crude extracts. The substrate for this enzyme is a small aromatic molecule that easily enters the bacterial cytoplasm and does not adversely affect cell viability.

In a high-throughput format, aliquots of bacterial cultures are incubated in the absence or presence of test compounds, and CDO activity is monitored by measuring absorbance at 375 nm following addition of catechol.

c) Specificity:

Compounds that score as positive in either the in vitro or in vivo assays described above are then tested for their effect on human RNA polyrnerase II. Those compounds which do not significantly inhibit human RNA polymerase II will be further developed as potential anti-tuberculosis agents.

What is claimed is:

1. An isolated and purified DNA encoding *M. tuberculosis* RNA polymerase alpha subunit wherein said DNA has a sequence selected from the group consisting of the sequence shown in FIGS. 3A and 3B, (SEQ. ID. NO. 4) and sequence-conservative variant thereof.

2. A DNA vector comprising the nucleic acid sequence of claim 1 operably linked to a transcription regulatory element.

3. A cell comprising a DNA vector as defined in claim 2, wherein said cell is selected from the group consisting of bacterial, fungal, plant, insect, and mammalian cells.

4. A cell as defined in claim 3, wherein said cell is a bacterial cell.

5. An isolated and purified polypeptide comprising a polypeptide identified by the amino acid sequence of SEQ. ID. NO. 5.

* * * * *

SEQUENCE LISTING

```
<160> NUMBER OF SEQ ID NOS:  15

<210> SEQ ID NO 1
<211> LENGTH: 59
<212> TYPE: PRT
<213> ORGANISM: M. tuberculosis

<400> SEQUENCE: 1

Ile Pro Gly Ala Ala Val Thr Ser Ile Arg Ile Asp Gly Val Leu His
1               5                   10                  15

Glu Phe Thr Thr Val Pro Gly Val Lys Glu Asp Val Thr Glu Ile Ile
            20                  25                  30

Leu Asn Leu Lys Ser Leu Val Val Ser Ser Glu Glu Asp Glu Pro Val
        35                  40                  45

Thr Met Tyr Leu Arg Lys Gln Gly Pro Gly Glu
    50                  55

<210> SEQ ID NO 2
<211> LENGTH: 76
<212> TYPE: PRT
<213> ORGANISM: B. subtilis

<400> SEQUENCE: 2

Leu Arg Arg Ile Leu Leu Ser Ser Leu Pro Gly Ala Ala Val Thr Ser
1               5                   10                  15

Ile Gln Ile Asp Gly Val Leu His Glu Phe Ser Thr Ile Glu Gly Val
            20                  25                  30

Val Glu Asp Val Thr Thr Ile Ile Leu His Ile Lys Lys Leu Ala Leu
```

-continued

```
        35                  40                  45

Lys Ile Tyr Ser Asp Glu Glu Lys Thr Leu Glu Ile Asp Val Gln Gly
    50                  55                  60

Glu Gly Thr Val Thr Ala Ala Asp Ile Thr His Asp
65                  70                  75

<210> SEQ ID NO 3
<211> LENGTH: 76
<212> TYPE: PRT
<213> ORGANISM: E. coli

<400> SEQUENCE: 3

Leu Arg Arg Ile Leu Leu Ser Ser Met Pro Gly Cys Ala Val Thr Glu
 1               5                  10                  15

Val Glu Ile Asp Gly Val Leu His Glu Tyr Ser Thr Lys Glu Gly Val
            20                  25                  30

Gln Glu Asp Ile Leu Glu Ile Leu Leu Asn Leu Lys Gly Leu Ala Val
        35                  40                  45

Arg Val Gln Gly Lys Asp Glu Val Ile Leu Thr Leu Asn Lys Ser Gly
    50                  55                  60

Ile Gly Pro Val Thr Ala Ala Asp Ile Thr His Asp
65                  70                  75

<210> SEQ ID NO 4
<211> LENGTH: 1230
<212> TYPE: DNA
<213> ORGANISM: M. tuberculosis

<400> SEQUENCE: 4
cgagtacccc caccttcggg ggcgccgccc ccgagtgccc ccacagacgt catatggcgg      60
acgtcgaaag gaagaagaaa caccatgctg atctcacagc gccccaccct gtccgaggac     120
gtcctcaccg acaaccgatc ccagttcgtg atcgaaccgc tggagccggg attcggctac     180
accctgggca attcgctgcg tcgcaccctg ctgtcgtcga ttcccggagc ggccgtcacc     240
agcattcgca tcgatggtgt acgcaccctg ctgtcgtcga ttcccggagc ggccgtcacc     300
agcattcgca tcgatggtgt actgcacgaa ttcaccacgg tgcccggggt caaagaagat     360
gtcaccgaga tcatcctgaa tctcaagagc ctggtggtgt cctcggagga ggacgagccg     420
gtcaccatgt acctacgcaa gcagggtccg ggtgaggtta ccgccggcga catcgtgccg     480
ccggccggcg tcaccgtgca caaccccggc atgcacatcg ccacgctgaa cgataagggc     540
aagctggaag tcgagctcgt cgtcgagcgt ggccgcggct atgtcccggc ggtgcaaaac     600
cgggcttcgg gtgccgaaat tgggcgcatt ccagtcgatt ccatctactc accggtgctc     660
aaagtgacct acaaggtgga cgccacccgg gtcgagcagc gcaccgactt cgacaagctg     720
atcctggacg tggagaccaa gaattcaatc agcccgcgcg acgcgctggc gtcggctggc     780
aagacgctgg tcgagttgtt cggcctggca cgggaactca acgtcgaggc cgaaggcatc     840
gagatcgggc cgtcgccggc cgaggccgat cacattgcgt cattcgccct gccgatcgac     900
gacctggatc tgacggtgcg gtcctacaac tgcctcaagc gcgagggggt gcacaccgtg     960
ggcgaactgg tggcgcgcac cgaatccgac ctgcttgaca tccgcaactt cggtcagaag    1020
tccatcgacg aggtgaagat caagctgcac cagctgggcc tgtcactcaa ggacagcccg    1080
ccgagcttcg acccctcgga ggtcgcgggc tacgacgtcg ccaccggcac ctggtcgacc    1140
gagggcgcgt acgacgagca ggactacgcc gaaaccgaac agctttagac tgcctctaat    1200
```

```
ccagacagga gcgtcagcta tgcccaagcc                                              1230
```

<210> SEQ ID NO 5
<211> LENGTH: 347
<212> TYPE: PRT
<213> ORGANISM: M. tuberculosis

<400> SEQUENCE: 5

```
Met Leu Ile Ser Gln Arg Pro Thr Leu Ser Glu Asp Val Leu Thr Asp
 1               5                  10                  15

Asn Arg Ser Gln Phe Val Ile Glu Pro Leu Pro Gly Phe Gly Tyr
            20                  25                  30

Thr Leu Gly Asn Ser Leu Arg Arg Thr Leu Leu Ser Ser Ile Pro Gly
        35                  40                  45

Ala Ala Val Thr Ser Ile Arg Ile Asp Gly Val Leu His Glu Phe Thr
50                  55                  60

Thr Val Pro Gly Val Lys Glu Asp Val Thr Glu Ile Ile Leu Asn Leu
65                  70                  75                  80

Lys Ser Leu Val Val Ser Ser Glu Glu Asp Glu Pro Val Thr Met Tyr
                85                  90                  95

Leu Arg Lys Gln Gly Pro Gly Glu Val Thr Ala Gly Asp Ile Val Pro
            100                 105                 110

Pro Ala Gly Val Thr Val His Asn Pro Gly Met His Ile Ala Thr Leu
        115                 120                 125

Asn Asp Lys Gly Lys Leu Glu Val Glu Leu Val Val Glu Arg Gly Arg
130                 135                 140

Gly Tyr Val Pro Ala Val Gln Asn Arg Ala Ser Gly Ala Glu Ile Gly
145                 150                 155                 160

Arg Ile Pro Val Asp Ser Ile Tyr Ser Pro Val Leu Lys Val Thr Tyr
                165                 170                 175

Lys Val Asp Ala Thr Arg Val Glu Gln Arg Thr Asp Phe Asp Lys Leu
            180                 185                 190

Ile Leu Asp Val Glu Thr Lys Asn Ser Ile Ser Pro Arg Asp Ala Leu
        195                 200                 205

Ala Ser Ala Gly Lys Thr Leu Val Glu Leu Phe Gly Leu Ala Arg Glu
210                 215                 220

Leu Asn Val Glu Ala Glu Gly Ile Glu Ile Gly Pro Ser Pro Ala Glu
225                 230                 235                 240

Ala Asp His Ile Ala Ser Phe Ala Leu Pro Ile Asp Asp Leu Asp Leu
                245                 250                 255

Thr Val Arg Ser Tyr Asn Cys Leu Lys Arg Glu Gly Val His Thr Val
            260                 265                 270

Gly Glu Leu Val Ala Arg Thr Glu Ser Asp Leu Leu Asp Ile Arg Asn
        275                 280                 285

Phe Gly Gln Lys Ser Ile Asp Glu Val Lys Ile Lys Leu His Gln Leu
290                 295                 300

Gly Leu Ser Leu Lys Asp Ser Pro Pro Ser Phe Asp Pro Ser Glu Val
305                 310                 315                 320

Ala Gly Tyr Asp Val Ala Thr Gly Thr Trp Ser Thr Glu Gly Ala Tyr
                325                 330                 335

Asp Glu Gln Asp Tyr Ala Glu Thr Glu Gln Leu
            340                 345
```

<210> SEQ ID NO 6
<211> LENGTH: 315

```
<212> TYPE: PRT
<213> ORGANISM: B. subtilis

<400> SEQUENCE: 6

Met Ile Glu Ile Glu Lys Pro Lys Ile Glu Thr Val Glu Ile Ser Asp
 1               5                  10                  15

Asp Ala Lys Phe Gly Lys Phe Val Val Glu Pro Leu Glu Arg Gly Tyr
            20                  25                  30

Gly Thr Thr Leu Gly Asn Ser Leu Arg Arg Ile Leu Leu Ser Ser Leu
        35                  40                  45

Pro Gly Ala Ala Val Thr Ser Ile Gln Ile Asp Gly Val Leu His Glu
    50                  55                  60

Phe Ser Thr Ile Glu Gly Val Val Glu Asp Val Thr Thr Ile Ile Leu
65                  70                  75                  80

His Ile Lys Lys Leu Ala Leu Lys Ile Tyr Ser Asp Glu Glu Lys Thr
                85                  90                  95

Leu Glu Ile Asp Val Gln Gly Glu Gly Thr Val Thr Ala Ala Asp Ile
            100                 105                 110

Thr His Asp Ser Asp Val Glu Ile Leu Asn Pro Asp Leu His Ile Ala
        115                 120                 125

Thr Leu Gly Glu Asn Ala Ser Phe Arg Val Arg Leu Thr Ala Gln Arg
    130                 135                 140

Gly Arg Gly Tyr Thr Pro Ala Asp Ala Asn Lys Arg Asp Asp Gln Pro
145                 150                 155                 160

Ile Gly Val Ile Pro Ile Asp Ser Ile Tyr Thr Pro Val Ser Arg Val
                165                 170                 175

Ser Tyr Gln Val Glu Asn Thr Arg Val Gly Gln Val Ala Asn Tyr Asp
            180                 185                 190

Lys Leu Thr Leu Asp Val Trp Thr Asp Gly Ser Thr Gly Pro Lys Glu
        195                 200                 205

Ala Ile Ala Leu Gly Ser Lys Ile Leu Thr Glu His Leu Asn Ile Phe
    210                 215                 220

Val Gly Leu Thr Asp Glu Ala Gln His Ala Phe Ile Met Val Glu Lys
225                 230                 235                 240

Glu Glu Asp Gln Lys Glu Lys Val Leu Glu Met Thr Ile Glu Glu Leu
                245                 250                 255

Asp Leu Ser Val Pro Ser Tyr Asn Cys Leu Lys Arg Ala Gly Ile Asn
            260                 265                 270

Thr Val Gln Glu Leu Ala Asn Lys Thr Phe Glu Asp Met Met Lys Val
        275                 280                 285

Arg Asn Leu Gly Arg Lys Ser Leu Glu Glu Val Lys Ala Lys Leu Glu
    290                 295                 300

Glu Leu Gly Leu Gly Ile Leu Arg Lys Asp Asp
305                 310                 315

<210> SEQ ID NO 7
<211> LENGTH: 328
<212> TYPE: PRT
<213> ORGANISM: M. genitalium

<400> SEQUENCE: 7

Met Glu Lys Phe Leu Lys Tyr Glu Ile Lys Val Asn Asn Asn Gln Pro
 1               5                  10                  15

Thr Asn Thr Asn Pro Asn Tyr Gly Ile Phe Glu Val Ala Pro Leu Glu
            20                  25                  30
```

Ser Gly Phe Gly Ile Thr Ile Gly Asn Ala Met Arg Arg Val Leu Leu
         35                  40                  45

Ser Cys Ile Pro Gly Ala Ser Val Phe Ala Ile Ala Ile Ser Gly Val
 50                  55                  60

Lys Gln Glu Phe Ser Asn Val Glu Gly Val Leu Glu Asp Val Thr Glu
 65                  70                  75                  80

Met Val Leu Asn Phe Lys Gln Leu Val Val Arg Ile Ser Asp Leu Leu
                 85                  90                  95

Phe Glu Asp Gly Glu Met Ile Glu Pro Pro Leu Glu Arg Trp Pro Val
                100                 105                 110

Leu Lys Val Thr Ala Glu Lys Lys Gly Ala Val Tyr Ala Lys Asp Leu
                115                 120                 125

Glu Cys Pro Ala Gly Phe Glu Val Ile Asn Lys Asp Leu Tyr Leu Phe
    130                 135                 140

Ser Leu Gln Lys Asp Met Lys Leu Thr Val Ser Val Tyr Val Lys Gln
145                 150                 155                 160

Gly Arg Gly Phe Thr Ser Phe Leu Glu Asn Arg Glu Leu Ile Asn Ser
                165                 170                 175

Leu Gly Ile Ile Ala Thr Asp Ala Asn Phe Ser Pro Val Leu His Cys
                180                 185                 190

Gly Tyr Glu Val Gln Val Lys Thr Ser Lys Gln Lys Leu Thr Asp
                195                 200                 205

His Leu Thr Phe Lys Ile Ala Thr Asn Gly Ala Ile Lys Ala Val Asp
    210                 215                 220

Ala Phe Ala Met Ala Ala Lys Ile Leu Ile Glu His Leu Asn Pro Ile
225                 230                 235                 240

Val Ser Val Asn Glu Ser Ile Lys Asn Leu Thr Ile Ile Gln Glu Lys
                245                 250                 255

Ala Glu Glu Arg Lys Val Lys Ser Phe Ala Lys Gln Ile Glu Glu Leu
                260                 265                 270

Asp Phe Thr Val Arg Thr Phe Asn Cys Leu Lys Arg Ser Gly Ile His
    275                 280                 285

Thr Leu Gln Glu Leu Leu Ser Lys Ser Leu Thr Asp Ile Arg Glu Ile
    290                 295                 300

Arg Asn Leu Gly Lys Lys Ser Glu Arg Glu Ile Ile Lys Lys Val Gln
305                 310                 315                 320

Glu Leu Gly Leu Lys Phe Arg Ser
                325

<210> SEQ ID NO 8
<211> LENGTH: 329
<212> TYPE: PRT
<213> ORGANISM: E. coli

<400> SEQUENCE: 8

Met Gln Gly Ser Val Thr Glu Phe Leu Lys Pro Arg Leu Val Asp Ile
 1               5                  10                  15

Glu Gln Val Ser Ser Thr His Ala Lys Val Thr Leu Glu Pro Leu Glu
                 20                  25                  30

Arg Gly Phe Gly His Thr Leu Gly Asn Ala Leu Arg Arg Ile Leu Leu
                 35                  40                  45

Ser Ser Met Pro Gly Cys Ala Val Thr Glu Val Glu Ile Asp Gly Val
     50                  55                  60

Leu His Glu Tyr Ser Thr Lys Glu Gly Val Gln Glu Asp Ile Leu Glu
 65                  70                  75                  80

```
Ile Leu Leu Asn Leu Lys Gly Leu Ala Val Arg Val Gln Gly Lys Asp
                85                  90                  95
Glu Val Ile Leu Thr Leu Asn Lys Ser Gly Ile Gly Pro Val Thr Ala
                100                 105                 110
Ala Asp Ile Thr His Asp Gly Asp Val Glu Ile Val Lys Pro Gln His
                115                 120                 125
Val Ile Cys His Leu Thr Asp Glu Asn Ala Ser Ile Ser Met Arg Ile
                130                 135                 140
Lys Val Gln Arg Gly Arg Gly Tyr Val Pro Ala Ser Thr Arg Ile His
145                 150                 155                 160
Ser Glu Glu Asp Glu Arg Pro Ile Gly Arg Leu Leu Val Asp Ala Cys
                165                 170                 175
Tyr Ser Pro Val Glu Arg Ile Ala Tyr Asn Val Glu Ala Ala Arg Val
                180                 185                 190
Glu Gln Arg Thr Asp Leu Asp Lys Leu Val Ile Glu Met Glu Thr Asn
                195                 200                 205
Gly Thr Ile Asp Pro Glu Glu Ala Ile Arg Arg Ala Ala Thr Ile Leu
                210                 215                 220
Ala Glu Gln Leu Glu Ala Phe Val Asp Leu Arg Asp Val Arg Gln Pro
225                 230                 235                 240
Glu Val Lys Glu Glu Lys Pro Glu Phe Asp Pro Ile Leu Leu Arg Pro
                245                 250                 255
Val Asp Asp Leu Glu Leu Thr Val Arg Ser Ala Asn Cys Leu Lys Ala
                260                 265                 270
Glu Ala Ile His Tyr Ile Gly Asp Leu Val Gln Arg Thr Glu Val Glu
                275                 280                 285
Leu Leu Lys Thr Pro Asn Leu Gly Lys Lys Ser Leu Thr Glu Ile Lys
                290                 295                 300
Asp Val Leu Ala Ser Arg Gly Leu Ser Leu Gly Met Arg Leu Glu Asn
305                 310                 315                 320
Trp Pro Pro Ala Ser Ile Ala Asp Glu
                325

<210> SEQ ID NO 9
<211> LENGTH: 329
<212> TYPE: PRT
<213> ORGANISM: H. influenza

<400> SEQUENCE: 9

Met Gln Gly Ser Val Thr Glu Phe Leu Lys Pro Arg Leu Val Asp Ile
1               5                   10                  15
Glu Gln Ile Ser Ser Thr His Ala Lys Val Ile Leu Glu Pro Leu Glu
                20                  25                  30
Arg Gly Phe Gly His Thr Leu Gly Asn Ala Leu Arg Arg Ile Leu Leu
                35                  40                  45
Ser Ser Met Pro Gly Cys Ala Val Thr Glu Val Glu Ile Asp Gly Val
                50                  55                  60
Leu His Glu Tyr Ser Ser Lys Glu Gly Val Gln Glu Asp Ile Leu Glu
65                  70                  75                  80
Val Leu Leu Asn Leu Lys Gly Leu Ala Val Lys Val Gln Asn Lys Asp
                85                  90                  95
Asp Val Ile Leu Thr Leu Asn Lys Ser Gly Ile Gly Pro Val Val Ala
                100                 105                 110
Ala Asp Ile Thr Tyr Asp Gly Asp Val Glu Ile Val Asn Pro Asp His
```

-continued

```
        115                 120                 125

Val Ile Cys His Leu Thr Asp Glu Asn Ala Ser Ile Ser Met Arg Ile
    130                 135                 140

Arg Val Gln Arg Gly Arg Gly Tyr Val Pro Ala Ser Ser Arg Thr His
145                 150                 155                 160

Thr Gln Glu Glu Arg Pro Ile Gly Arg Leu Leu Val Asp Ala Cys Tyr
                165                 170                 175

Ser Pro Val Glu Arg Ile Ala Tyr Asn Val Glu Ala Ala Arg Val Glu
            180                 185                 190

Gln Arg Thr Asp Leu Asp Lys Leu Val Ile Glu Leu Glu Thr Asn Gly
        195                 200                 205

Ala Leu Glu Pro Glu Glu Ala Ile Arg Arg Ala Ala Thr Ile Leu Ala
    210                 215                 220

Glu Gln Leu Asp Ala Phe Val Asp Leu Arg Asp Val Arg Gln Pro Glu
225                 230                 235                 240

Ile Lys Glu Glu Lys Pro Glu Phe Xaa Asp Pro Ile Leu Leu Arg Pro
                245                 250                 255

Val Asp Asp Leu Glu Leu Thr Val Arg Ser Ala Asn Cys Leu Lys Ala
            260                 265                 270

Glu Thr Ile His Tyr Ile Gly Asp Leu Val Gln Arg Thr Glu Val Glu
        275                 280                 285

Leu Leu Lys Thr Pro Asn Leu Gly Lys Lys Ser Leu Thr Glu Ile Lys
    290                 295                 300

Asp Val Leu Ala Ser Arg Gly Leu Ser Leu Gly Met Arg Leu Glu Asn
305                 310                 315                 320

Trp Pro Pro Ala Ser Ile Ala Glu Asp
                325

<210> SEQ ID NO 10
<211> LENGTH: 328
<212> TYPE: PRT
<213> ORGANISM: B. pertusis

<400> SEQUENCE: 10

Met Ser Thr Gln Gly Phe Leu Lys Pro Arg Ser Ile Glu Val Glu Pro
 1               5                  10                  15

Val Gly Ala His His Ala Lys Ile Val Met Glu Pro Phe Glu Arg Gly
            20                  25                  30

Tyr Gly His Thr Leu Gly Asn Ala Leu Arg Arg Ile Leu Leu Ser Ser
        35                  40                  45

Met Thr Gly Tyr Ala Pro Thr Glu Val Gln Met Thr Gly Val Val His
    50                  55                  60

Glu Tyr Ser Thr Ile Ala Gly Val Arg Glu Asp Val Val Asp Ile Leu
65                  70                  75                  80

Leu Asn Leu Lys Gly Val Val Phe Lys Leu His Asn Arg Asp Glu Val
                85                  90                  95

Thr Leu Val Leu Arg Lys Asn Gly Ala Gly Ala Val Val Ala Ser Asp
            100                 105                 110

Ile Glu Leu Pro His Asp Val Glu Ile Ile Asn Pro Asp His Leu Ile
        115                 120                 125

Cys Asn Leu Thr Asp Ala Gly Lys Ile Glu Met Gln Val Lys Val Glu
    130                 135                 140

Lys Gly Arg Gly Tyr Val Pro Gly Asn Val Arg Ala Leu Ser Glu Asp
145                 150                 155                 160
```

```
Arg Thr His Thr Ile Gly Arg Ile Val Leu Asp Ala Ser Phe Ser Pro
                165                 170                 175

Val Arg Arg Val Ser Tyr Ala Val Glu Ser Ala Arg Val Glu Gln Arg
            180                 185                 190

Thr Asp Leu Asp Lys Leu Val Leu Asp Ile Glu Thr Asn Gly Val Ile
        195                 200                 205

Ser Pro Glu Glu Ala Val Arg Gln Ala Ala Arg Ile Leu Met Asp Gln
    210                 215                 220

Ile Ser Val Phe Ala Ala Leu Glu Gly Ala Gly Asp Ala Tyr Glu Pro
225                 230                 235                 240

Pro Val Arg Gly Thr Pro Gln Ile Asp Pro Val Leu Leu Arg Pro Val
                245                 250                 255

Asp Asp Leu Glu Leu Thr Val Arg Ser Ala Asn Cys Leu Lys Ala Glu
            260                 265                 270

Asn Ile Tyr Tyr Ile Gly Asp Leu Ile Gln Arg Thr Glu Asn Glu Leu
        275                 280                 285

Leu Lys Thr Pro Asn Leu Gly Arg Lys Ser Leu Asn Glu Ile Lys Glu
    290                 295                 300

Val Leu Ala Ala Arg Gly Leu Thr Leu Gly Met Lys Leu Glu Asn Trp
305                 310                 315                 320

Pro Pro Leu Gly Leu Glu Arg Pro
                325

<210> SEQ ID NO 11
<211> LENGTH: 329
<212> TYPE: PRT
<213> ORGANISM: S. typhimurium

<400> SEQUENCE: 11

Met Gln Gly Ser Val Thr Glu Phe Leu Lys Pro Arg Leu Val Asp Ile
1               5                   10                  15

Glu Gln Val Ser Ser Thr His Ala Lys Val Thr Leu Glu Pro Leu Glu
            20                  25                  30

Arg Gly Phe Gly His Thr Leu Gly Asn Ala Leu Arg Arg Ile Leu Leu
        35                  40                  45

Ser Ser Met Pro Gly Cys Ala Val Thr Glu Val Glu Ile Asp Gly Val
    50                  55                  60

Leu His Glu Tyr Ser Thr Lys Glu Gly Val Gln Glu Asp Ile Leu Glu
65                  70                  75                  80

Ile Leu Leu Asn Leu Lys Gly Leu Ala Val Arg Val Gln Gly Lys Asp
                85                  90                  95

Glu Val Ile Leu Thr Leu Asn Lys Ser Gly Ile Gly Pro Val Thr Ala
            100                 105                 110

Ala Asp Ile Thr His Asp Gly Asp Val Glu Ile Val Lys Pro Gln His
        115                 120                 125

Val Ile Cys His Leu Thr Asp Glu Asn Ala Ser Ile Ser Met Arg Ile
    130                 135                 140

Lys Val Gln Arg Gly Arg Gly Tyr Val Pro Ala Ser Thr Arg Ile His
145                 150                 155                 160

Ser Glu Glu Asp Glu Arg Pro Ile Gly Arg Leu Leu Val Asp Ala Cys
                165                 170                 175

Tyr Ser Pro Val Glu Arg Ile Ala Tyr Asn Val Glu Ala Ala Arg Val
            180                 185                 190

Glu Gln Arg Thr Asp Leu Asp Lys Leu Val Ile Glu Met Glu Thr Asn
        195                 200                 205
```

```
Gly Thr Ile Asp Pro Glu Glu Ala Ile Arg Arg Ala Ala Thr Ile Leu
    210                 215                 220

Ala Glu Gln Leu Glu Ala Phe Val Asp Leu Arg Asp Val Arg Gln Pro
225                 230                 235                 240

Glu Val Lys Glu Lys Pro Glu Phe Asp Pro Ile Leu Leu Arg Pro
                245                 250                 255

Val Asp Asp Leu Glu Leu Thr Val Arg Ser Ala Asn Cys Leu Lys Ala
                260                 265                 270

Glu Ala Ile His Tyr Ile Gly Asp Leu Val Gln Arg Thr Glu Val Glu
                275                 280                 285

Leu Leu Lys Thr Pro Asn Leu Gly Lys Lys Ser Leu Thr Glu Ile Lys
    290                 295                 300

Asp Val Leu Ala Ser Arg Gly Leu Ser Leu Gly Met Arg Leu Glu Asn
305                 310                 315                 320

Trp Pro Pro Ala Ser Ile Ala Asp Glu
                325

<210> SEQ ID NO 12
<211> LENGTH: 379
<212> TYPE: PRT
<213> ORGANISM: C. trachomitis

<400> SEQUENCE: 12

Met Ser Asp Ser Ser His Asn Leu Leu Tyr Asn Lys Phe Glu Leu Pro
1               5                   10                  15

Glu Ser Val Lys Met Ser Pro Val Glu Gly Ala Val Gly Ser Ile Asp
                20                  25                  30

Lys Val Ala Arg Phe Val Ala Asp Pro Leu Glu Lys Gly Met Gly His
            35                  40                  45

Thr Leu Gly Ser Ala Leu Arg Arg Ala Leu Leu Ile Gly Leu Glu Ala
        50                  55                  60

Pro Ala Ile Val Ser Phe Ser Met Thr Gly Val Leu His Glu Tyr Met
65                  70                  75                  80

Ala Val Glu Gly Ile Ile Glu Asp Val Thr Asn Met Leu Leu Asn Leu
                85                  90                  95

Lys Gly Ser Leu Leu Lys Lys Tyr Pro Leu Gln Asp Cys Glu Gly Gly
            100                 105                 110

Arg Cys Ser Gln Lys Leu Arg Ala Thr Ile Ser Val Asp Ala Ser Asp
        115                 120                 125

Leu Ala Ala Ala Gly Gly Gln Lys Glu Val Thr Leu Gly Asp Leu Leu
    130                 135                 140

Gln Glu Gly Thr Phe Glu Ala Val Asn Pro Glu His Val Ile Phe Thr
145                 150                 155                 160

Val Thr Arg Pro Met Gln Leu Glu Val Met Leu Arg Val Ala Phe Gly
                165                 170                 175

Arg Gly Tyr Ser Pro Ser Glu Arg Ile Val Leu Glu Glu Arg Gly Met
            180                 185                 190

Asn Glu Ile Val Leu Asp Ala Phe Ser Pro Val Val Leu Val Asn Tyr
        195                 200                 205

Phe Val Glu Asp Thr Arg Val Gly Gln Asp Thr Asp Phe Asp Arg Leu
    210                 215                 220

Val Leu Gln Val Glu Thr Asp Gly Arg Val Ala Pro Lys Glu Ala Val
225                 230                 235                 240

Ala Phe Ala Thr Gln Ile Leu Ser Lys His Phe Ser Val Phe Glu Lys
```

-continued

```
                245                 250                 255

Met Asp Glu Lys Arg Ile Val Phe Glu Glu Ala Ile Ser Val Glu Lys
            260                 265                 270

Glu Asn Lys Asp Asp Ile Leu His Lys Leu Val Leu Gly Ile Asn Glu
        275                 280                 285

Ile Glu Leu Ser Val Arg Leu Ile Arg Ser Thr Asn Cys Leu Ser Asn
    290                 295                 300

Ala Asn Ile Glu Thr Ile Gly Glu Leu Val Ile Met Pro Glu Pro Arg
305                 310                 315                 320

Leu Leu Gln Phe Arg Asn Phe Gly Lys Lys Ser Leu Cys Glu Ile Lys
                325                 330                 335

Asn Lys Leu Lys Glu Met Lys Leu Glu Leu Gly Met Asp Leu Ser Gln
            340                 345                 350

Phe Gly Val Gly Leu Asp Asn Val Lys Glu Lys Met Lys Trp Tyr Ala
        355                 360                 365

Glu Lys Ile Arg Ser Ser Lys Asn Thr Lys Ala
    370                 375

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 13
ctacgcaagc agggtccggg tgag                                          24

<210> SEQ ID NO 14
<211> LENGTH: 24
<212> TYPE: DNA
<213> ORGANISM: Artificial Sequence
<220> FEATURE:
<223> OTHER INFORMATION: :

<400> SEQUENCE: 14
ctcacccgga ccctgcttgc gtag                                          24

<210> SEQ ID NO 15
<211> LENGTH: 64
<212> TYPE: DNA
<213> ORGANISM: M. tuberculosis

<400> SEQUENCE: 15
agcttgcaga tctagcgatc gcagccgacg tgatacctga ccgttgttga tagtgtcggc   60
ggct                                                                64
```